(12) United States Patent
Fujimoto et al.

(10) Patent No.: US 8,785,141 B2
(45) Date of Patent: Jul. 22, 2014

(54) BACTERIAL TOXIN ADSORBING MATERIAL, METHOD OF REMOVING THE TOXIN BY ADSORBING, AND AN ADSORBER FORMED BY FILLING THE ADSORBING MATERIAL THEREIN

(75) Inventors: Tamiji Fujimoto, Settsu (JP); Fumiyasu Hirai, Amagasaki (JP); Shigeo Furuyoshi, Kobe (JP)

(73) Assignee: Kaneka Corporation, Osaka (JP)

( * ) Notice: Subject to any disclaimer, the term of this patent is extended or adjusted under 35 U.S.C. 154(b) by 2741 days.

(21) Appl. No.: 10/362,534

(22) PCT Filed: Aug. 24, 2001

(86) PCT No.: PCT/JP01/07240
§ 371 (c)(1),
(2), (4) Date: Nov. 16, 2004

(87) PCT Pub. No.: WO02/15964
PCT Pub. Date: Feb. 28, 2002

(65) Prior Publication Data
US 2008/0213523 A1    Sep. 4, 2008

(30) Foreign Application Priority Data

Aug. 25, 2000    (JP) ................. 2000-254840

(51) Int. Cl.
| | | |
|---|---|---|
| *G01N 1/30* | (2006.01) | |
| *G01N 33/53* | (2006.01) | |
| *C12Q 1/00* | (2006.01) | |
| *C12N 11/00* | (2006.01) | |
| *G01N 33/569* | (2006.01) | |
| *B01J 20/20* | (2006.01) | |
| *A61M 1/36* | (2006.01) | |
| *B01J 20/28* | (2006.01) | |
| *B01J 20/26* | (2006.01) | |

(52) U.S. Cl.
CPC ... *B01J 20/26* (2013.01); *B01J 20/20* (2013.01); *A61M 1/3679* (2013.01); *B01J 20/28078* (2013.01); *A61M 1/3627* (2013.01); *B01J 20/264* (2013.01); *B01J 20/261* (2013.01)
USPC ............. 435/7.33; 435/4; 435/6.15; 435/7.2; 435/7.32; 435/7.8; 435/7.92; 435/29; 435/30; 435/31; 435/32; 435/40.5; 435/173.1; 435/173.4; 435/173.9; 435/174

(58) Field of Classification Search
None
See application file for complete search history.

(56) References Cited

U.S. PATENT DOCUMENTS

| | | | |
|---|---|---|---|
| 4,769,450 | A | 9/1988 | Stone et al. |
| 2009/0259072 | A1 | 10/2009 | Umehara et al. |

FOREIGN PATENT DOCUMENTS

| | | | | |
|---|---|---|---|---|
| EP | 0 834 350 A1 | * | 7/1997 | ............... B01J 39/04 |
| EP | 0 800 862 A1 | | 10/1997 | |

(Continued)

OTHER PUBLICATIONS

Amberlite Xad Polymeric Resins, Product Information Sheet from Sigma-Aldrich. Mar. 20, 1998.*

(Continued)

*Primary Examiner* — Ja'na Hines
(74) *Attorney, Agent, or Firm* — Novak Druce Connolly Bove + Quigg LLP

(57) ABSTRACT

The invention aims at providing an adsorbent for bacterial toxins, a method for removal of such toxins by adsorption, and an adsorber packed with said adsorbent.
Provided are an adsorbent for bacterial toxins,
which comprises a water-insoluble porous material having a mode of pore radius of 20 angstroms to 1,000 angstroms, a method for removal of bacterial toxins using said adsorbent, and an adsorber packed with said adsorbent.

1 Claim, 1 Drawing Sheet

(56) References Cited

FOREIGN PATENT DOCUMENTS

| | | | | |
|---|---|---|---|---|
| EP | 0800862 A1 | * 10/1997 | ............... | B01J 20/26 |
| EP | 0834350 A1 | 4/1998 | | |
| JP | 57017658 | 1/1982 | | |
| JP | 01016389 | 3/1989 | | |
| JP | 1181875 | 7/1989 | | |
| JP | 03045657 A | 2/1991 | | |
| JP | 05-058903 A | 3/1993 | | |
| JP | 6312017 | 8/1994 | | |
| JP | 06-312017 A | 11/1994 | | |
| JP | 7000816 | 6/1995 | | |
| JP | 8319431 | 3/1996 | | |
| JP | 08-173803 | 7/1996 | | |
| JP | 08-257115 A | 10/1996 | | |
| JP | 08-257398 A | 10/1996 | | |
| JP | 10-85328 | 4/1998 | | |
| JP | 10290833 | 4/1998 | | |
| JP | 10-147533 | 6/1998 | | |
| JP | 10-290833 | * 11/1998 | ............... | A61K 1/36 |
| JP | 10-290833 A | 11/1998 | | |
| WO | WO-96/20042 A1 | 7/1996 | | |

OTHER PUBLICATIONS

Sueoka. Therapeutic Apheresis. 1997. vol.(1)3:271-283); Adsorbent, Part 3).*
Nagaki et al., (J. Med. Microbiol. 1991. vol. 38, pp. 354-359).*
Sawada et al., (J. Hyg. Camb. 1986. vol. 97:103-114).*
Bio Rad Laboratories. AffiPrep Polymyxin Matrix, 25 ml. Catalog No. 156-0010. Life Science Group.*
Strickler et al., (J. of Clin. Microbio. 1989. vol. 27(5) 1031-1035).*
WPI/Thomson 1991-104938 for JP03-045657.
WPI/Thomson 1993-121280 for JP 05-058903.
WPI/Thomson 1995-027288 for JP06-312017.
WPI/Thomson 1982-18598E for JP57-017658.

* cited by examiner

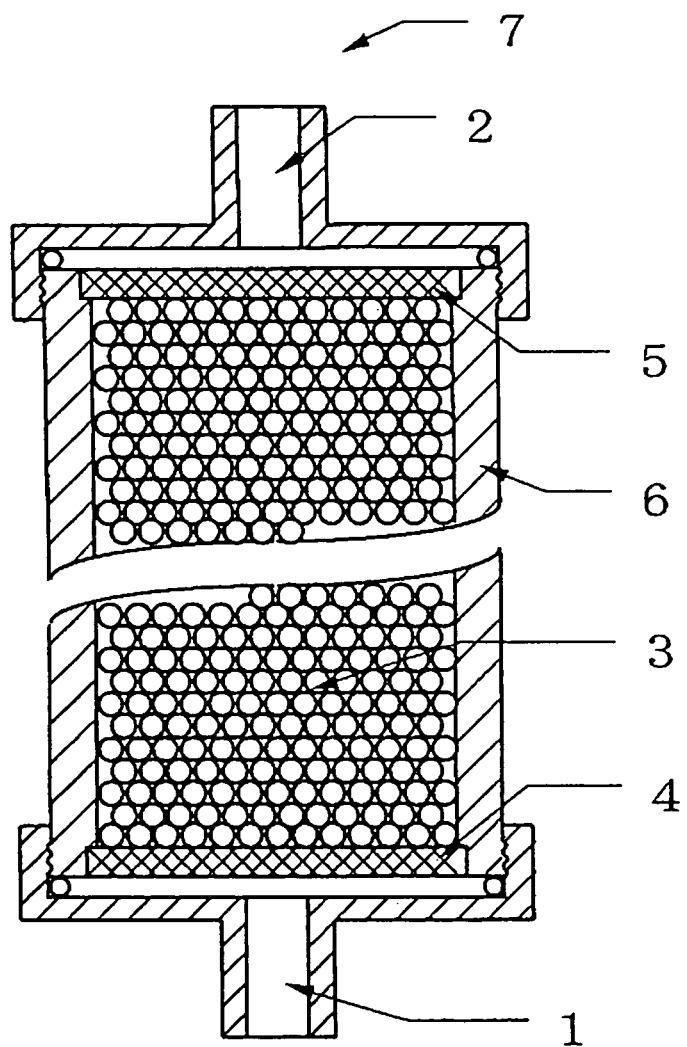

BACTERIAL TOXIN ADSORBING MATERIAL, METHOD OF REMOVING THE TOXIN BY ADSORBING, AND AN ADSORBER FORMED BY FILLING THE ADSORBING MATERIAL THEREIN

CROSS REFERENCE TO RELATED APPLICATIONS

This application is a National Stage of PCT/JP2001/07240 filed Aug. 24, 2001 which in turn claims priority from Japanese Application 2000-254840 filed Aug. 25, 2000.

TECHNICAL FIELD

The present invention relates to an adsorbent for bacterial toxins, a method for removal of such toxins by adsorption, and an adsorber packed with said adsorbent.

BACKGROUND ART

A bacterial toxin may be defined as "a substance which is a bacterial metabolite or constituent and causes, in a trace amount, an unfavorable response in the living body". Bacterial toxins are roughly classified into two classes, endotoxins and exotoxins, according to the site of occurrence. The former are also called as protein toxins, and the latter as lipopolysaccharides (hereinafter referred to as "LPSs"). There are a large number of bacterial toxins, and the number of such toxins so far known now stands at about 200. Typical examples are cholera toxin, staphylococcal α toxin, botulinum toxin, tetanus toxin, enterotoxin (10 species are already known, namely staphylococcal enterotoxin A, B, C1, C2, C3, D, E, G, H, and I; hereinafter referred to as SEA, SEB, SEC1, SEC2, SEC3, SED, SEE, SEG, SEH, and SEI, respectively), verotoxins, diphtheria toxin, pertussis toxin, Toxic shock syndrome toxin-1 (hereinafter referred to as TSST-1), and endotoxins.

Among these, enterotoxins and TSST-1 are also called as superantigens.

In the case of an ordinary antigen, it is taken up by an antigen-presenting cell and fragmented (into peptides composed of 10 to 15 amino acids) therein, and an antigen fragment, in the form bound to a pocket site of a MHC (major histocompatibility complex) class II molecule, is presented on the antigen-presenting cell surface. This is recognized by the α chain and β chain of the TCR (T cell receptor) of a specific T cell clone, and the T cell is activated and the immune response goes on.

On the other hand, in the case of a superantigen, the antigen is not fragmented but binds directly to a MHC class II molecule on the antigen-presenting cell. This is further recognized by the TCR on a T cell, whereby the T cell is activated. On that occasion, the antigen is recognized through a specific Vβ region of the TCR. Unlike ordinary antigens, that antigen is recognized by almost all members of a T cell population expressing this specific Vβ region, and T cells are thereby activated and causing cytokine production.

Thus, when an individual is exposed to a superantigen, a huge number of T cells are activated as compared with the ordinary specific immune response and the release of a cytokine, for instance, occurs in a short period of time, supposedly causing an abnormal reaction(s) in the living body.

Known as the superantigen are TSST-1, enterotoxins and exfoliative toxin A (exfoliative A: ETA) produced by *Staphylococcus aureus*, which is a gram-positive bacterium, and exotoxins produced by streptococci (streptococcal pyrogenic exotoxin A, B, C: SPE-A, SPE-B, SPE-C), among others.

An enterotoxin is one of toxins produced by bacteria. It has various biological activities, such as emetic, pyrogenic and mitogenic activities, and causes food poisoning symptoms or Toxic shock syndrome (hereinafter referred to as TSS). "Enterotoxin" is a term formed from "entero", which means the intestine, and toxin. Although it essentially means a toxin causing diarrhea, it has not yet established that an enterotoxin causes diarrhea; hence what it really means is unclear.

Toxins having enterotoxin activity include toxins having various biological activities, such as emetic, pyrogenic and mitogenic activities, and causing food poisoning symptoms or TSS. Known among them are enterotoxins produced by staphylococci, heat-labile enterotoxin (hereinafter referred to as LT) produced by *Campylobacter* species, and LT and heat-stable enterotoxin (ST) produced by enterotoxigenic *Escherichia coli*, among others.

Staphylococci are widely distributed on or in the skin, nasal cavity, oral cavity, pharynx, urinary organs and intestinal tract of various animals including humans and, further, in air, sewage, river, food, and so forth and include a large number of species. Among such a large number of *Staphylococcus* species, it is coagulase-positive *Staphylococcus aureus* (hereinafter referred to as *S. aureus*) that shows pathogenicity in humans. *S. aureus* causes various infectious diseases, such as TSS and staphylococcal scaled skin syndrome (SSSS) and, as pathogens, producing problems such as hospital infections. Furthermore, *Staphylococcus epidermidis*, for instance, may cause endocarditis, meningitis, septicemia, etc., and *Staphylococcus saprophticus* may cause urinary tract infection, although they are coagulase-negative.

Known staphylococcal pathogenic factors include various toxins, enzymes and other biologically active substances, such as Clumping factor, fibrinogen-binding protein, fibrinogen-binding protein A, fibrinogen-binding protein B, collagen-binding protein, coagulase, polysaccharide/adhesin, polysaccharide intracellular adhesin, 220-kDa adhesin, SEA, SEB, SEC1, SEC2, SEC3, SED, SEE, SEG, SEH, SEI, TSST-1, exfoliative toxin A, exfoliative toxin B, protein A, lipase, V8 protease, fatty acid modifying enzyme, panton-valentine leucocidin, leucocidin R, capsular polysaccharide, staphylokinase, α-toxin, β-hemolysin, γ-hemolysin, δ-hemolysin, phospholipase C, metalloprotease (elastase), and hyaluronidase.

These bacterial toxins cause a great variety of diseases, from such relatively slight ones as food poisoning and traveler's diarrhea to such severe ones possibly leading to death as lethal diarrhea, tetanus, pertussis, botulism, diphtheria, cholera, TSS, and septicemia.

In the case of septicemia and TSS, for instance, antibiotics, γ-globulin preparations and so forth are used in the treatment thereof, but the mortality is still high. As for food poisoning, it is difficult to perfectly prevent the occurrence of food poisoning how much care is taken from the hygienic point of view and, further, even when a food sufficiently heated is taken, it may cause food poisoning if a heat-stable toxin, such as an enterotoxin, is already contained therein.

As regards the removal of superantigens by adsorption, Japanese Kokai Publication Hei-8-319431 discloses an adsorbent having a specific side chain. However, this cannot be said to be satisfactory from the capacity viewpoint.

The present inventors have previously found that a material with a compound having a log P value (P being the partition coefficient in the octanol-water system) of not less than 2.50 as immobilized thereon can well adsorb TSST-1 (one of bacterial toxins) (Japanese Kokai Publication Hei-10-290833). For preparing such adsorbent material, however, a number of steps are required.

When, for instance, antibodies specific to various toxins respectively are used, it is indeed possible to remove toxins from body fluids such as blood, plasma and serum, culture supernatants, foodstuffs, and drinks, but these have disadvantages, namely they are expensive and, when sterilized, they are denatured and their absorptive ability is markedly reduced.

As regards endotoxins, various adsorbents are known for removing them from body fluids. For example, Japanese Kokoku Publication Hei-1-16389 discloses an adsorbent comprising polymyxin, which is known as an antidote against endotoxins, immobilized on an appropriate carrier. This adsorbent is effective against infections with gram negative bacteria but the removal of endotoxins alone cannot be expected to be highly effective against infections with gram positive bacteria or multiple infections with gram positive and gram negative bacteria.

Furthermore, in recent years, it has been revealed that TSST-1, as a superantigen, activates the immune system and enhances the endotoxin toxicity to a level thousands of times higher. Therefore, the occurrence of an endotoxin at a low concentration, at which septicemia will not be caused clinically, is indicated to cause septicemia.

Accordingly, the advent of a highly effective adsorbent for bacterial toxins, which can be produced in an inexpensive and simple and easy manner, is earnestly desired.

SUMMARY OF THE INVENTION

It is an object of the present invention to provide an adsorbent for bacterial toxins which is free of such drawbacks of the prior art, a method for removal of such toxins by adsorption, and an adsorber packed with said adsorbent.

As a result of intensive investigations for overcoming the above-mentioned disadvantages, the present inventors could discover that when a water-insoluble porous material, which has a mode of pore radius of 20 angstroms to 1,000 angstroms, is used, bacterial toxins can be adsorbed at very high rates. The present invention, therefore, is directed to an adsorbent for bacterial toxins, which comprises a water-insoluble porous material having a mode of pore radius of 20 angstroms to 1,000 angstroms.

DETAILED DISCLOSURE OF THE INVENTION

In search of a compound effective in adsorbing bacterial toxins, the present inventors evaluated various water-insoluble materials or modifications thereof for bacterial toxin adsorbing ability. As a result, it was found that water-insoluble porous materials, which have a mode of pore radius of 20 angstroms to 1,000 angstroms, are suited for use as adsorbents for bacterial toxins. When an adsorbent having a mode of pore radius of not more than 20 angstroms is used, the capacity for adsorbing bacterial toxins is insufficient; this lowers its utility. When an adsorbent having a mode of pore radius not less than 1,000 angstroms is used, proteins (mainly albumin) other than bacterial toxins are adsorbed in large amounts, resulting in a substantial decrease in the amount of bacterial toxins adsorbed; the utility thus lowers from the selectivity viewpoint. Therefore, the water-insoluble porous material to be used in the present invention preferably has a mode of pore radius of from 20 angstroms to 1,000 angstroms, more preferably from 40 angstroms to 600 angstroms, most preferably from 50 angstroms to 400 angstroms.

The water-insoluble porous material according to the invention is a material internally having a porous structure, occurring as a solid at ordinary temperature and ordinary pressure and having a very low solubility in water.

The porous structure of the water-insoluble porous material can be expressed in terms of pore volume, specific surface area, and pore size distribution, among others. These indices can be determined, for example, by the gas adsorption method based on the adsorption isotherm for a gas such as nitrogen, mercury porosimetry using a mercury porosimeter, electron microscopy, and small angle X-ray scattering ("Takoshitsutai no Seishitsu to sono Oyo-gijutsu (Porous Materials, Properties and Application Technology)", pages 248 to 288, edited by Yasushi Takeuchi, published by Fujitec Corporation). It is generally considered that mercury porosimetry is preferred for the so-called macropores, namely pores having a pore size of 100 angstroms and larger, and the gas adsorption method for the so-called micropores, namely pores having a pore size of 100 angstroms or smaller, although strict division is impossible.

However, pores may be deformed by the pressure applied on the occasion of mercury porosimetry depending on the properties of the material in question. Therefore, it is necessary to select an adequate measurement method taking the physical properties of the material into consideration.

The pore size distribution is generally shown in a graphic form, the pore radius (e.g. in angstroms) on the X-axis and the value (e.g. in mL/g-angstrom) derived, by differentiation, from the cumulative pore volume (e.g. in mL/g) on the Y-axis. The mode is the value corresponding to the highest frequency in the distribution. Thus, the mode of pore radius according to the invention means the pore radius corresponding to the maximum differentiated cumulative pore volume in the pore size distribution determined by such a measurement method as mentioned above.

The form of the water-insoluble porous material according to the invention includes, but is not limited to, granules, plates, fibers, and hollow fibers, among others. The size is not particularly restricted, either.

The water-insoluble porous material to be used as the adsorbent in the invention is preferably a hydrophobic inorganic material such as active carbon, an organic material intermediate in polarity such as an acrylic material, a hydrophobic organic material such as a polystyrene-based material, or an organic-organic, organic-inorganic or the like composite material resulting from a combination of the materials mentioned above. A polystyrene-based material, which is a hydrophobic organic material, is more preferred.

The polystyrene-based material so referred to herein includes such polymer materials as polymers mainly made of styrene and/or a derivative thereof. Thus, it may be a homopolymer of styrene or a derivative thereof, or a copolymer containing polymer constituent(s) other than styrene as well, including a copolymer with divinylbenzene and/or a derivative thereof.

The acrylic material so referred to herein includes such polymer compounds as polymers mainly made of acrylic acid, methacrylic acid, and/or a derivative thereof. Thus, it may be a homopolymer of an acrylic or a derivative thereof, or a copolymer containing a polymer constituent(s) other than acrylics as well. It is an organic material intermediate in polarity. Polyacrylamide, which is a hydrophilic organic material, is excluded, however. Among acrylic polymers, methacrylate ester resins are particularly preferred.

Furthermore, active carbon and a substance similar thereto, according to the invention, indicates any of active or activated carbon species in general use or a water-insoluble porous material having a carbonized surface. Morphologically, active carbon species are classified into powdery active carbon, granular active carbon, fibrous active carbon, molded active carbon and so forth. The raw materials thereof are diverse and include, but are not limited to, vegetable ones such as wood chips and wastes from sugar manufacture, mineral ones such as peat and petroleum pitch, synthetic materials such as acrylic resins and phenol resins, and natural materials such as seaweed and grain, among others. Their sizes are not particularly restricted, either.

For the purpose of improving the blood compatibility of the material, this may be treated or modified, to the extent not detracting from its adsorptive affinity for bacterial toxins, by introducing an appropriate side chain or ligand into the material or coating the same with a hydrophilic material, for instance. Examples of the side chain or ligand include, but are not limited to, those having a hydroxyl and/or amino group(s), and the hydrophilic material includes, but is not limited to, polymers of hydroxyethyl methacrylate, and cellulose. However, in cases where the mode of pore radius is within the above-specified range, the effects of the invention can be achieved without such treatment.

The bacterial toxin according to the invention is "a substance which is a bacterial metabolite or constituent and causes, in a trace amount, an unfavorable response in the living body" and includes, but is not limited to, El Tor hemolysin of *Vibrio cholerae*, streptococcal streptolysin O, streptococcal streptolysin S, staphylococcal α toxin, *Pseudomonas aeruginosa* leucocidin, botulinum toxin, tetanus toxin, enterotoxigenic *Escherichia coli* heat-stable enterotoxin, *Vibrio parahaemoliticus* heat-stable hemolysin, verotoxins, diphtheria toxin, pertussis toxin, coagulase, exfoliatin, tetrodotoxin, TSST-1, endotoxins, etc.

The superantigen according to the invention indicates a substance capable of activating a huge number of T cells as compared with the ordinary specific immune response to thereby cause an abnormal reaction(s) in the living body. It includes, but is not limited to, TSST-1, enterotoxins and exfoliative toxin A (exfoliative A: ETA) produced by *S. aureus*, and exotoxins produced by streptococci (streptococcal pyrogenic exotoxin A, B, C: SPE-A, SPE-B, SPE-C), among others.

The toxin having enterotoxin activity according to the invention means a toxin having various biological activities, such as emetic, pyrogenic and mitogenic activities, and causing food poisoning symptoms or TSS. It includes, but is not limited to, enterotoxins produced by staphylococci, LT produced by *Campylobacter*, and LT and heat-stable enterotoxin (ST) produced by enterotoxigenic *Escherichia coli*, among others.

The staphylococcal pathogenic factor according to the invention indicates a substance produced by staphylococci and causing an abnormal response(s) in the living body. It includes, but is not limited to, various toxins, enzymes and other biologically active substances, such as Clumping factor, fibrinogen-binding protein, fibrinogen-binding protein A, fibrinogen-binding protein B, collagen-binding protein, coagulase, polysaccharide/adhesin, polysaccharide intracellular adhesin, 220-kDa adhesin, SEA, SEB, SEC1, SEC2, SEC3, SED, SEE, SEG, SEH, SEI, TSST-1, exfoliative toxin A, exfoliative toxin B, protein A, lipase, V8 protease, fatty acid modifying enzyme, panton-valentine leucocidin, leucocidine R, capsular polysaccharide, staphylokinase, α-toxin, β-hemolysin, γ-hemolysin, δ-hemolysin, phospholipase C, metalloprotease (elastase), and hyaluronidase.

The adsorbent according to the invention is excellent in bacterial toxin adsorbing capacity, in particular in adsorbing superantigens, toxins having enterotoxin activity, and staphylococcal pathogenic factors.

The adsorbent for bacterial toxins according to the invention is suited for use in removing, by adsorption, bacterial toxins from body fluids, culture supernatants, foodstuffs, and drinks, in particular removing, by adsorption, bacterial toxins from body fluids.

The body fluid according to the invention includes blood, plasma, serum, ascitic fluid, lymph, synovia fluid, fractions obtained from these, and other humoral components derived from the living body.

The method for removal, by adsorption, of bacterial toxins from a body fluid using the adsorbent of the invention includes various techniques. The most expedient one comprises drawing out the body fluid, storing the same in a bag or the like, admixing the same with the adsorbent and, after removal of *S. aureus* and/or other bacterial toxins, recovering the bacterial toxin-free body fluid by filtering off the adsorbent. Another technique comprises filling the adsorbent in a container having a body fluid inlet and a body fluid outlet and equipped, at least at the outlet, with a filter allowing the passage of the body fluid but preventing the passage of the adsorbent, and passing the body fluid through the same. While either technique is useful, the latter is more expedient from the procedural viewpoint. When the container is incorporated in an extracorporeal circulation circuit, bacterial toxins can be removed efficiently from the body fluid, in particular blood, of a patient in an on-line manner.

The extracorporeal circulation circuit so referred to herein may comprise the adsorbent of the invention alone or a combination thereof with another extracorporeal circulation system for treatment. An example of the system to be used combinedly is an artificial dialysis circuit, and the adsorbent can be used in combination with dialysis therapy.

Now, the adsorber for bacterial toxins according to the invention, in which the above-mentioned adsorbent for bacterial toxins is used, is described referring to FIG. 1 schematically showing, in cross section, an example of the adsorber. In FIG. 1, 1 indicates a body fluid inlet, 2 a body fluid outlet, 3 the adsorbent for bacterial toxins according to the invention, 4 and 5 each a filter for preventing the adsorbent from flowing out, 6 a column, and 7 the adsorber for bacterial toxins. However, the adsorber for bacterial toxins is not limited to such specific example but may have any constitution provided that it comprises a container having a fluid inlet and a fluid outlet and equipped with a device for preventing the adsorbent for bacterial toxins from flowing out of the container and the above-mentioned adsorbent packed therein.

The above flowing-out preventing device may be a filter made of a mesh, nonwoven fabric, or cotton plug, for instance. The shape, material, and size of the container are not particularly restricted. As for the shape, a cylindrical one is preferred, however. Preferred as the container material are materials resistant to sterilization treatment, specifically including silicone-coated glass, polypropylene, polyvinyl chloride, polycarbonate, polysulfone, polymethylpentene, and the like. The capacity of the container is preferably 50 to 1,500 ml, more preferably 100 to 800 ml, most preferably 150 to 400 ml, and the diameter thereof is preferably 2 to 20 cm, more preferably 3 to 15 cm, most preferably 4 to 10 cm.

BRIEF DESCRIPTION OF THE DRAWING

FIG. 1 is a schematic representation, in cross section, of an example of the adsorber for bacterial toxins according to the invention.

EXPLANATION OF THE SYMBOLS

1: body fluid inlet
2: body fluid outlet

3: adsorbent for bacterial toxins
4 and 5: filters for preventing the adsorbent from flowing out
6: column
7: adsorber for bacterial toxins.

BEST MODES FOR CARRYING OUT THE INVENTION

The following examples illustrate the present invention in further detail. They are, however, by no means limitative of the scope of the invention.

EXAMPLE 1

Using a styrene-divinylbenzene copolymer (DIAION HP-20: product of Mitsubishi Chemical Corporation) as the adsorbent for bacterial toxins, the following experiment was carried out. This material is an adsorbent having a mode of pore radius within the range of 100 angstroms to 200 angstroms. Pore sizes were determined by mercury porosimetry.

TSST-1 (product of Toxin Technologies, Inc.) was used as a bacterial toxin, and the adsorbent was evaluated for its capacity for adsorbing the toxin in fetal bovine serum (FBS). The TSST-1 concentration used was about 5 ng/mL.

Thus, 0.2 mL of the above adsorbent and 1.2 mL of TSST-1-containing FBS were blended, and the mixture was shaken at 37° C. for 2 hours. Thereafter, the supernatant was separated from the adsorbent and assayed for the TSST-1 concentration in the supernatant by ELISA (Enzyme Linked Immuno Sorbent Assay).

The ELISA of TSST-1 was carried out as follows. Rabbit anti-TSST-1 IgG (product of Toxin Technologies), a primary antibody, was 1600-fold diluted with a coating buffer, and the dilution was distributed in 100-μl portions into wells of a microplate. After overnight standing at 4° C., the plate was washed. A 3% bovine serum albumin solution was distributed in 200-μl portions into the wells of the microplate and, after 2 hours of standing at room temperature, the microplate was washed. Then, 100 μl each of a standard TSST-1 solution and the supernatant before or after incubation were added to each well of the microplate. After 2 hours of standing at room temperature, the plate was washed. Rabbit anti-TSST-1 HRP (product of Toxin Technologies), a secondary antibody, was 400-fold diluted with a 1% bovine serum albumin solution, and the dilution was distributed in 100-μl portions into the wells. After 2 hours of standing at room temperature, the plate was washed. An orthophenylenediamine solution was distributed in 100-μl portions into the wells, followed by 10 minutes of standing at room temperature. 4 N sulfuric acid was distributed in 100-μl portions into the wells, followed by absorbance measurement at 492 nm. The TSST-1 concentrations in the supernatant before and after incubation were determined by comparison with the absorbance of the standard solution.

EXAMPLE 2

A styrene-divinylbenzene copolymer (DIAION HP-40: product of Mitsubishi Chemical Corporation) was used as the adsorbent for bacterial toxins and evaluated for its capacity for adsorbing TSST-1 under the same conditions as in Example 1. This material is an adsorbent having a mode of pore radius within the range of 200 angstroms to 300 angstroms. Pore sizes were determined by mercury porosimetry.

EXAMPLE 3

A styrene-divinylbenzene copolymer (DIAION HP-50: product of Mitsubishi Chemical Corporation) was used as the adsorbent for bacterial toxins and evaluated for its capacity for adsorbing TSST-1 under the same conditions as in Example 1. This material is an adsorbent having a mode of pore radius within the range of 900 angstroms to 1,000 angstroms. Pore sizes were determined by mercury porosimetry.

EXAMPLE 4

A styrene-divinylbenzene copolymer (DIAION SP-875: product of Mitsubishi Chemical Corporation) was used as the adsorbent for bacterial toxins and evaluated for its capacity for adsorbing TSST-1 under the same conditions as in Example 1. This material is an adsorbent having a mode of pore radius within the range of 20 angstroms to 30 angstroms. Pore sizes were determined by nitrogen gas adsorption method.

EXAMPLE 5

A methacrylate ester resin (Amberlite XAD-7: product of Organo Corporation) was used as the adsorbent for bacterial toxins and evaluated for its capacity for adsorbing TSST-1 under the same conditions as in Example 1. This material is an adsorbent having a mode of pore radius within the range of 500 angstroms to 600 angstroms. Pore sizes were determined by mercury porosimetry.

EXAMPLE 6

Petroleum pitch-derived spherical active carbon was used as the adsorbent for bacterial toxins and evaluated for its capacity for adsorbing TSST-1 under the same conditions as in Example 1. This material is an adsorbent having a mode of pore radius within the range of 20 angstroms to 30 angstroms. Pore sizes were determined by nitrogen gas adsorption method.

COMPARATIVE EXAMPLE 1

The same volume as the adsorbent of physiological saline and TSST-1-added FBS were mixed up, and the mixture was subjected to the same evaluation as in Example 1.

The results of Examples 1 to 6 and Comparative Example 1 are shown in Table 1. The percent adsorption was calculated as follows:

Percent adsorption (%)=100×(concentration in Comparative Example 1−concentration in the example)/concentration in Comparative Example 1

TABLE 1

|  | TSST-1 concentration after shaking (ng/mL) | Percent adsorption (%) |
| --- | --- | --- |
| Example 1 | 0.06 | 98.8 |
| Example 2 | 0.45 | 90.8 |
| Example 3 | 3.81 | 22.2 |
| Example 4 | 3.39 | 30.8 |
| Example 5 | 1.38 | 71.8 |
| Example 6 | 4.30 | 12.2 |
| Comparative Example 1 | 4.90 | — |

EXAMPLE 7

Using a styrene-divinylbenzene copolymer (DIAION HP-20: product of Mitsubishi Chemical Corporation) as the adsorbent for bacterial toxins, the following experiment was carried out. This material is an adsorbent having a mode of pore radius within the range of 100 angstroms to 200 angstroms. Pore sizes were determined by mercury porosimetry.

Among the enterotoxins, SEA, SEB, SEC1, CED, and SEE (products of Toxin Technologies) were used as bacterial toxins, and the adsorbent was evaluated for its capacity of adsorbing them in fetal bovine serum (FBS).

Thus, 0.2 mL of the above adsorbent and 1.2 mL of FBS containing an appropriate amount of one of the enterotoxins were blended, and the mixture was shaken at 37° C. for 2 hours. Thereafter, the supernatant was separated from the adsorbent and assayed for the enterotoxin concentration in the supernatant using an ELISA kit (product of r-Biopharm).

COMPARATIVE EXAMPLE 2

The same volume as the adsorbent of physiological saline and FBS containing one of the enterotoxins were mixed up, and the mixture was subjected to the same evaluation as in Example 7.

The results of Example 7 and Comparative Example 2 are shown in Table 2. The percent adsorption was calculated as follows:

Percent adsorption (%)=100×(concentration in Comparative Example 2−concentration in Example 7)/concentration in Comparative Example 2

TABLE 2

| | Concentration after shaking (ng/ml) | | Percent adsorption (%) |
| --- | --- | --- | --- |
| | Example 7 | Comparative Example 2 | |
| SEA | 0.23 | 1.17 | 80 |
| SEB | 0.22 | 2.80 | 92 |
| SEC1 | 0.08 | 0.50 | 83 |
| SED | 0.10 | 1.47 | 93 |
| SEE | 0.06 | 1.80 | 97 |

INDUSTRIAL APPLICABILITY

According to the invention, it is possible to remove, by adsorption, bacterial toxins with good efficiency by using an adsorbent for bacterial toxins which is characterized in that it is made of a water-insoluble porous material having a mode of pore radius of 20 angstroms to 1,000 angstroms.

The invention claimed is:

1. The method for removal of exotoxin by adsorption, which comprises the step of contacting an adsorbent with a bacterial toxin-containing fluid, wherein the adsorbent comprises a water-insoluble porous material having a mode of pore radius of 100 angstroms to 600 angstroms, and wherein the water-insoluble porous material comprises a polystyrene-based material, wherein the exotoxin is selected from the group consisting of Toxic shock syndrome toxin-1, staphylococcal enterotoxin B, staphylococcal enterotoxin C1, staphylococcal enterotoxin D, and staphylococcal enterotoxin E, wherein the polystyrene-based material does not have a side chain or ligand.

* * * * *